United States Patent
Sgroi, Jr.

(10) Patent No.: US 10,463,374 B2
(45) Date of Patent: Nov. 5, 2019

(54) ADAPTER ASSEMBLY FOR A FLEXIBLE CIRCULAR STAPLER

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 307 days.

(21) Appl. No.: 15/466,897

(22) Filed: Mar. 23, 2017

(65) Prior Publication Data

US 2017/0333044 A1    Nov. 23, 2017

Related U.S. Application Data (60) Provisional application No. 62/337,564, filed on May 17, 2016.

(51) Int. Cl.
| | | |
|---|---|---|
| *A61B 17/115* | (2006.01) | |
| *A61B 17/072* | (2006.01) | |
| *A61B 17/34* | (2006.01) | |
| *A61B 17/00* | (2006.01) | |
| *A61B 90/00* | (2016.01) | |

(52) U.S. Cl.
CPC ........ *A61B 17/1155* (2013.01); *A61B 17/072* (2013.01); *A61B 17/34* (2013.01); *A61B 2017/0046* (2013.01); *A61B 2017/00292* (2013.01); *A61B 2017/00367* (2013.01); *A61B 2017/00398* (2013.01); *A61B 2017/00477* (2013.01); *A61B 2017/07257* (2013.01); *A61B 2017/07271* (2013.01); *A61B 2090/0813* (2016.02)

(58) Field of Classification Search
CPC .... A61B 17/072; A61B 17/34; A61B 17/1155
USPC ..................... 227/176.1, 19, 175.1
See application file for complete search history.

(56) References Cited

U.S. PATENT DOCUMENTS

| | | |
|---|---|---|
| 2,777,340 A | 1/1957 | Hettwer et al. |
| 2,957,353 A | 10/1960 | Babacz |

(Continued)

FOREIGN PATENT DOCUMENTS

| | | |
|---|---|---|
| CA | 2451558 A1 | 1/2003 |
| CN | 2500264 Y | 7/2002 |

(Continued)

OTHER PUBLICATIONS

European Examination Report dated Jan. 24, 2019, issued in EP Appln. No. 17 171 270.

(Continued)

*Primary Examiner* — Nathaniel C Chukwurah (57) ABSTRACT

An adapter assembly for a flexible circular stapler including a pusher assembly, a trocar assembly, a first drive assembly and a second drive assembly. The pusher assembly includes a pusher member, a puller member, and first and second pulley members. The trocar assembly includes a trocar member operably disposed relative to the pusher assembly. The first drive assembly includes a first cable for advancing and retracting the trocar member relative to the pusher assembly, and the second drive assembly includes a second cable for retracting the puller member to cause rotation of the first and second pulley members. Rotation of the first and second pulley members causes advancement of the pusher member.

18 Claims, 7 Drawing Sheets

(56) References Cited

U.S. PATENT DOCUMENTS

| | | | |
|---|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,271,543 A * | 12/1993 | Grant .................. A61B 17/115 227/179.1 |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A * | 5/1995 | Bessler ............... A61B 17/1114 227/179.1 |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |

(56) References Cited

U.S. PATENT DOCUMENTS

| | | |
|---|---|---|
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 * | 9/2011 | Whitman .......... A61B 17/115 227/155 |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |

(56) References Cited

U.S. PATENT DOCUMENTS

| | | |
|---|---|---|
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1* | 12/2012 | Malkowski ............ A61B 17/29 606/1 |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 1547454 A | 11/2004 |
| CN | 1957854 A | 5/2007 |
| CN | 101495046 A | 7/2009 |
| CN | 102247182 A | 11/2011 |
| DE | 102008053842 A1 | 5/2010 |
| EP | 0427949 A1 | 5/1991 |
| EP | 0705571 A1 | 4/1996 |
| EP | 1563793 A1 | 8/2005 |

(56) References Cited

FOREIGN PATENT DOCUMENTS

| | | |
|---|---|---|
| EP | 1769754 A1 | 4/2007 |
| EP | 2316345 A1 | 5/2011 |
| EP | 2668910 A2 | 12/2013 |
| EP | 3108828 A2 | 12/2016 |
| ES | 2333509 A1 | 2/2010 |
| JP | 2005-125075 A | 5/2005 |
| KR | 20120022521 A | 3/2012 |
| WO | 2011/108840 A2 | 9/2011 |
| WO | 2012/040984 A1 | 4/2012 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
European Search Report dated Sep. 28, 2017, issued in EP Appln. No. 17171270.

* cited by examiner

FIG. 9 ion No. 62/337,564 filed May 17,
ADAPTER ASSEMBLY FOR A FLEXIBLE CIRCULAR STAPLER

CROSS-REFERENCE TO RELATED APPLICATIONS

This application claims the benefit of and priority to U.S. Provisional Patent Application No. 62/337,564 filed May 17, 2016, the entire disclosure of which is incorporated by reference herein.

BACKGROUND

Technical Field

The present disclosure relates to surgical stapler devices. More particularly, the present disclosure relates to adapter assemblies for flexible circular staplers.

Background of Related Art

Circular staplers are used to perform end to end anastomosis. A typical circular stapler includes an anvil assembly releasably securable relative to a cartridge assembly disposed on a distal end of an elongate shaft. Operation of the circular stapler requires actuation of a handle assembly disposed on a proximal end of the elongate shaft to first retract the anvil assembly relative to the cartridge assembly to clamp tissue, and then to advance or push one or more actuation assemblies to staple and cut tissue. The flexibility of the elongate shaft of the circular stapler is limited because of the rigidity of the drive shafts required for actuation of the pusher assemblies.

Accordingly, it would be beneficial to have a circular stapler in which operation of one or more actuation assemblies is achieved using cables, whereby a flexibility of the circular stapler is increased.

SUMMARY

An adapter assembly for a flexible circular stapler is provided. The adapter assembly includes a pusher assembly, a trocar assembly, a first drive assembly, and a second drive assembly. The pusher assembly includes a pusher member, a puller member for retracting the pusher member, and first and second pulley members operably disposed between the pusher member and the puller member. The trocar assembly includes a trocar member operably disposed relative to the pusher assembly. The first drive assembly includes a first cable for advancing and retracting the trocar member relative to the pusher assembly. The second drive assembly includes a second cable for retracting the puller member to cause rotation of the first and second pulley members. Rotation of the first and second pulley members causes advancement of the pusher member.

In embodiments, the first and second pulley members are connected to the puller member by respective first and second connectors. The first and second connectors may be wrapped around the respective first and second pulley members prior to advancement of the pusher member. Each of the first and second pulley members may include a least a first gear for engaging the pusher member. The pusher member may be configured to staple tissue upon the advancement thereof. The trocar member may be releasably securable to an anvil assembly. A third drive assembly includes a third cable connected to the pusher member.

In some embodiments, the third drive assembly is configured to cause retraction of the pusher member upon operation thereof. Each of the first and second pulley members may include a coating for maintaining tension on the respective first and second connectors. Each of the first and second pulley members may include a torsion spring for maintaining tension on the respective first and second connectors. The adapter assembly may include an elongate body and a coupling assembly supported on a proximal end of the elongate body. The adapter assembly may include a loading unit supported on a distal end of the elongate body. The loading unit may include a staple cartridge supporting a plurality of staples. At least a portion of the elongate body of the adapter assembly is flexible. The elongate body may include an inner flexible coil and an outer sheath.

Also provided is a circular stapler including an actuation assembly, and an adapter assembly operably secured to the actuation assembly for stapling tissue.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the disclosure are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

Figure 1:
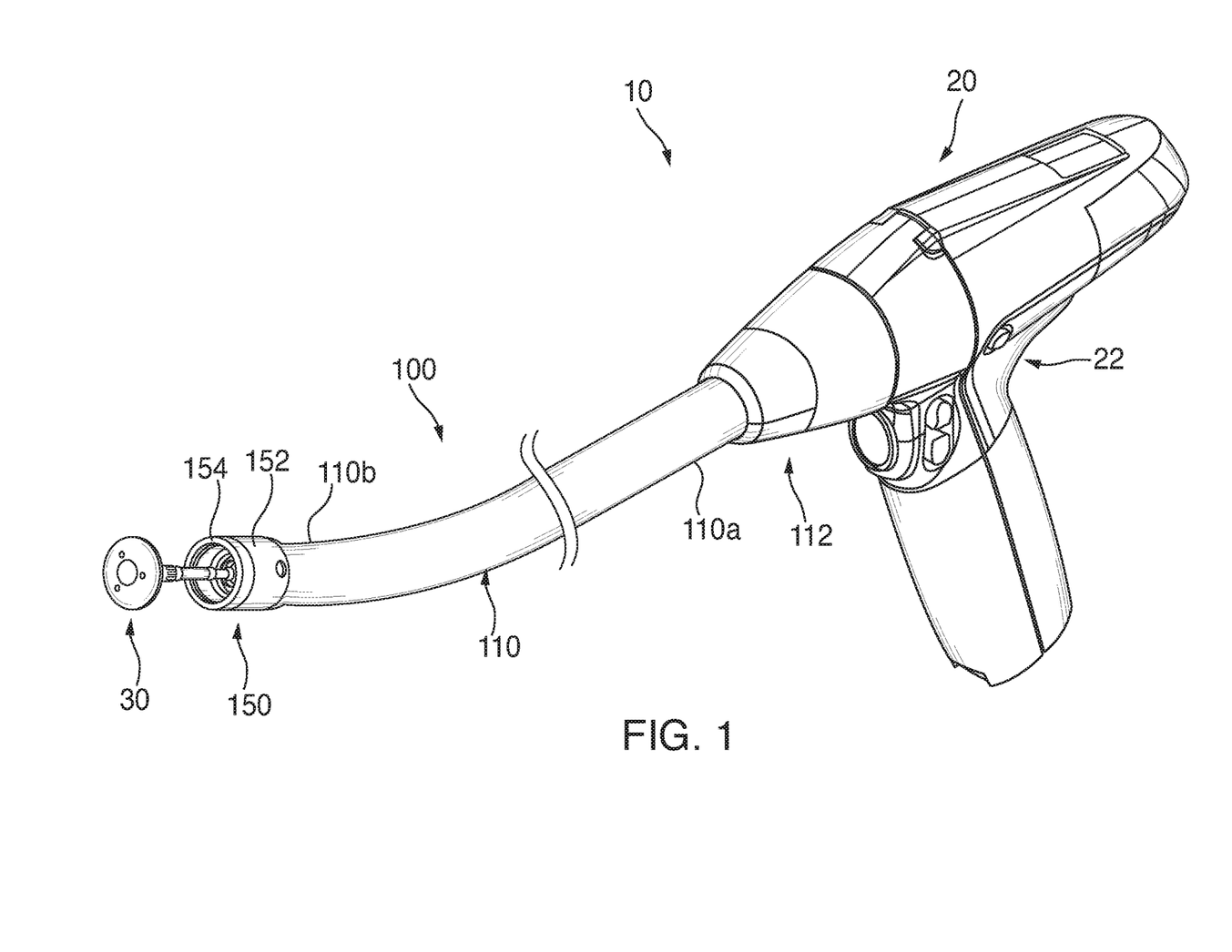
FIG. 1 is a side perspective view of a circular stapling apparatus including an adapter assembly according to an embodiment of the present disclosure.
Figure 2:
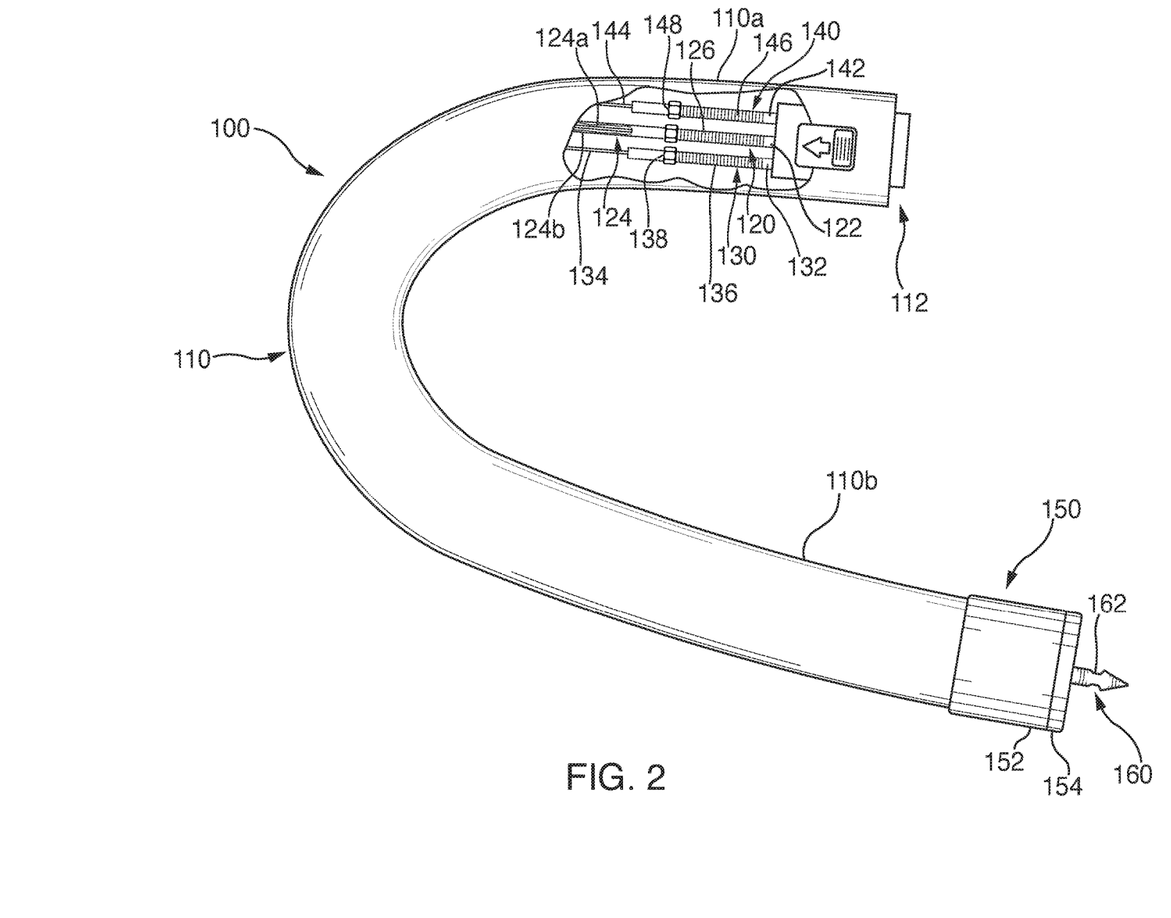
FIG. 2 is a top perspective schematic view of the adapter assembly and loading unit shown in FIG. 1, with a partial cutaway.

With reference to FIGS. 1 and 2, an adapter assembly in accordance with an embodiment of the present disclosure, shown generally as adapter assembly 100, is configured for selective connection to a powered handheld electromechanical instrument shown, generally as actuation assembly 20. As illustrated in FIG. 1, the actuation assembly 20 is configured for selective connection with the adapter assembly 100, and, in turn, the adapter assembly 100 is configured for selective connection with an anvil assembly 30. Collectively, the adapter assembly 100, the actuation assembly 20, and the anvil assembly 30, form a surgical stapling device 10.

For a detailed description of the structure and function of an exemplary electromechanical instrument, please refer to commonly owned U.S. Pat. No. 9,055,943, the content of which is incorporated by reference herein in its entirety.

With continued reference to FIGS. 1 and 2, the adapter assembly 100 includes an elongate body 110, and a coupling assembly 112 supported on a proximal end 110a of the elongate body 110 for securing the elongate body 110 to the actuation assembly 20. As shown, the elongate body 110 includes an inner flexible coil 111a (FIG. 3), and a protective outer sheath 111b (FIG. 3), however, the elongate body 110 may be formed from rigid memory metal, semi-flexible material, bellows, and/or from any suitable material. The construction of the elongate body 110 permits the adapter assembly 100 to bend and/or flex along its length such that the loading unit 150 may be selectively moved relative to the actuation assembly 10 (FIG. 1) to facilitate positioning of the loading unit 150 within a patient (not shown). It is envisioned the elongated body 110 may formed of, for example, etc.

The adapter assembly 100 further includes first, second, and third drive assemblies or power screws 120, 130, 140 (FIG. 2) extending through the elongate body 110, and a loading unit 150 secured to a distal end 110b of the elongate body 110. Although shown as being integrally formed with the elongate body 110, it is envisioned that the loading unit 150 may be at least partially releasable from the elongate body 110 to permit reuse of the adapter assembly 100.

The coupling assembly 112 of the adapter assembly 100 is configured to releasably secure adapter assembly 100 to the actuation assembly 20. As shown, the actuation assembly 20 (FIG. 1) includes a powered handle assembly 22. As will become apparent from the following disclosure, the actuation assembly 20 may include any mechanism suitable for actuating each of the first, second, and third drive assemblies 120, 130, 140. Each of the first, second, and third drive assemblies 120, 130, 140 may be actuated by the same drive member (not shown), or as will be described in more detail below, each of the first, second, and third drive assemblies 120, 130, 140 are actuated by respective first, second, and third drive members (not shown).

With continued reference to FIG. 2, the first drive assembly 120 is configured to effect a first function of the adapter assembly 100, e.g., advance and retract a trocar member 162 of a trocar assembly 160 of the adapter assembly 100. The second drive assembly 130 is configured to effect a second function of the adapter assembly 100, e.g., advancement of a pusher member 172 (FIG. 3) of a pusher assembly 170 (FIG. 3) of the loading unit 150. The third drive assembly 140 is configured to effect a third function of the adapter assembly 100, e.g., retraction of the pusher member 172 of the pusher assembly 170 of the loading unit 150. Each of the first, second, and third drive assemblies 120, 130, 140 includes a respective first, second, and third drive shaft 122, 132, 142, which is operably connectable to a respective first, second, or third drive member (not shown) of the actuation assembly 20.

With continued reference to FIG. 2, the first drive assembly 120 includes a cable, e.g., a first push/pull cable 124, that is secured to the trocar member 162 of the trocar assembly 160 to approximate the anvil assembly 30 (FIG. 1) relative to a staple cartridge 152 of the loading unit 150 prior to actuation of the loading unit 150, and to move the anvil assembly 30 away from the staple cartridge 154 of the loading unit 150 following a stapling procedure. The first cable 124 includes an inner wire or braided wires 124a, and an outer sheath 124b supporting the inner wire 124a. For example, the inner wire 124a may be a stainless steel braided cable, and the outer sheath 124b may be a spring winding wrapped around the braided cable. Both the inner wire 124a and the outer sheath 124b are flexible to accommodate the flexion of the elongate body 110 of the adapter assembly 100.

The first drive assembly 120 further includes a first screw member 126 operably connected to the first drive shaft 122, and a first carriage member or nut 128 longitudinally disposed about the first screw member 126. It is envisioned that the first drive shaft 122 and the first screw member 126 may be integrally formed. A proximal end of the inner wire 124a of the first cable 124 is secured to the first carriage member 128 such that longitudinal movement of the first carriage member 128 causes longitudinal movement of the inner wire 124a of the first cable 124.

The second drive assembly 130 includes a respective cable, e.g., second cable 134. The second cable 134 may include a flexible wire, cable, ribbon, string, or any other similar material. The second cable 134 is secured to a puller member 174 (FIG. 3) of the pusher assembly 170 (FIG. 3) to move the puller member 174 proximally during operation of the surgical stapling device 10. As will be described in further detail below, retraction of the puller member 174 causes the pusher member 172 of the pusher assembly 170 to advance. As the pusher assembly 170 is advanced, staples "S" are ejected from the staple cartridge 152 of the loading unit 150 and are formed against anvil assembly 30 (FIG. 1).

The second drive assembly 130 further includes a second screw member 136 operably connected to the second drive shaft 132, and a second carriage member or nut 138 longitudinally disposed about the second screw member 136. It is envisioned that the second drive shaft 132 and the second screw member 136 may be integrally formed. A proximal end of the second cable 134 is operably connected to the second carriage member 138 such that longitudinal movement of the second carriage member 138 causes longitudinal movement of the second cable 134.

The third drive assembly 140 includes a respective cable, e.g., third cable 144. The third cable 144 may include a flexible wire, cable, ribbon, string, or any other similar material. As will be described in further detail below, the third cable 144 is secured to the pusher member 172 (FIG. 3) of the pusher assembly 170 (FIG. 3) to retract the pusher member 172 subsequent to the advancement of the pusher member 172 of the pusher assembly 170.

The third drive assembly 140 further includes a third screw member 146 operably connected to the third drive shaft 142, and a third carriage member or nut 148 longitudinally disposed about the third screw member 146. It is envisioned that the third drive shaft 142 and the third screw member 146 may be integrally formed. A proximal end of the third cable 144 is operably connected to the first carriage member 128. Longitudinal movement of the third carriage member 138 causes longitudinal movement of the third cable 144. A distal end of the third cable 144 is secured to the pusher member 172.

As each of the second and third drive assemblies 130, 140 need only operate in a single direction, i.e., retraction of respective puller member 174 and pusher member 172, it is envisioned that either or both of the second and third drive assemblies 130, 140 may include an uptake pulley (not shown) around which the respective second or third cables 134, 144 are wound to cause the retraction of respective puller member 174 and pusher member 172. It is further envisioned that the adapter assembly 100 may be modified such that the first drive assembly 120 operates in only a single direction and/or the second and third drive assemblies 130, 140 operate in two directions, e.g., push/pull directions.

Figure 3:
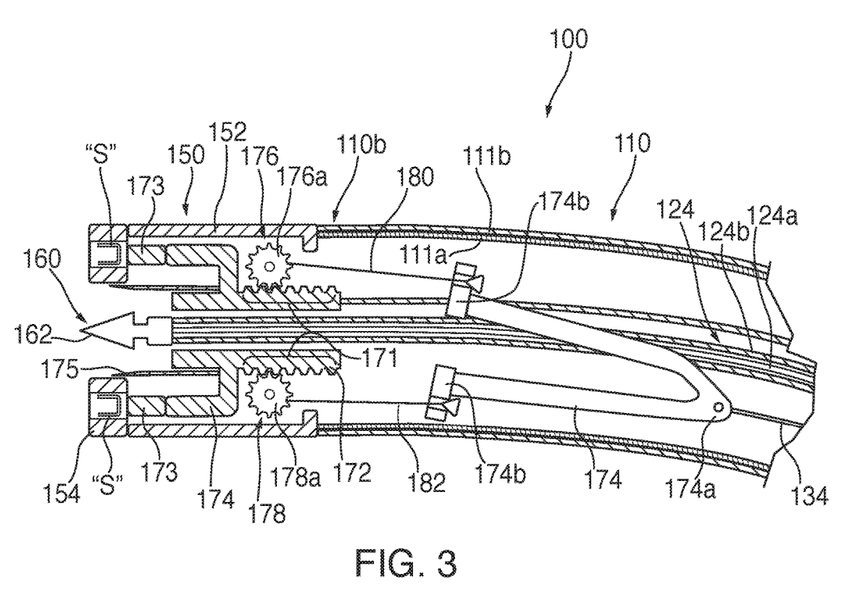
FIG. 3 is a side cross-sectional schematic view of a distal end of the adapter assembly and loading unit shown in FIG. 1.

With particular reference to FIG. 3, the loading unit 150 is supported on the distal end 110b of the elongate body 110. As noted above, the loading unit 150 may be integrally formed with the elongate body 110 or may be releasably secured thereto to permit reuse of the adapter assembly 100. The loading unit 150 includes a shell member 152, a staple cartridge 154 supported on the shell member 152, and the pusher assembly 170 operably supported within the shell member 152. The staple cartridge 154 of the loading unit 150 is configured to dispense a circular array of staples "S". The staple cartridge 154 may be removable from the shell member 152 to permit replacement of the staple cartridge 154 following a stapling procedure such that the adapter assembly 100 and/or the loading unit 150 may be reused.

With continued reference to FIG. 3, the trocar assembly 160 includes the trocar member 162 supported on a distal end of the first cable 124 and extends through the shell member 152 and the pusher assembly 170 of the loading unit 150. The trocar member 162 is configured to releasably engage the anvil assembly 30 (FIG. 1). As noted above, the first drive assembly 120 is configured to retract and advance the trocar member 162. It is envisioned that the trocar assembly 160 may include a spring for facilitating one of advancement and retraction of the trocar member 162 such that the first drive assembly 120 need only operate in a single direction.

The pusher assembly 170 includes the pusher member 172, the puller member 174, and an activation assembly, e.g., first and second pulley members 176, 178. The pusher member 172 includes an annular base portion 172a defining a plurality of notches or rack gear teeth 171 disposed along an outer surface thereof. The plurality of notches 171 may extend entirely around the annular base portion 172a of the pusher member 172, or may instead be positioned to correspond with the first and second pulley members 176, 178. A plurality of fingers 173 corresponding to staples "S" within the staple cartridge 154 extend distally from the annular base portion 172a of the pusher member 172 for ejecting the staples "S" from the staple cartridge 154. The pusher member 172 further includes a circular knife 175 for cutting tissue (not shown).

With continued reference to FIG. 3, the puller member 174 of the pusher assembly 170 of the loading unit 150 includes a substantially U-shaped body having a proximal end 174a to which the second cable 134 is secured, and a bifurcated distal end 174b to which first and second connectors 180, 182 are secured. Although shown including the bifurcated distal end 174b for accommodating the first and second connectors 180, 182, the distal end 174b of the puller member 174 may be configured to accommodate any number of connectors.

Figure 4A:
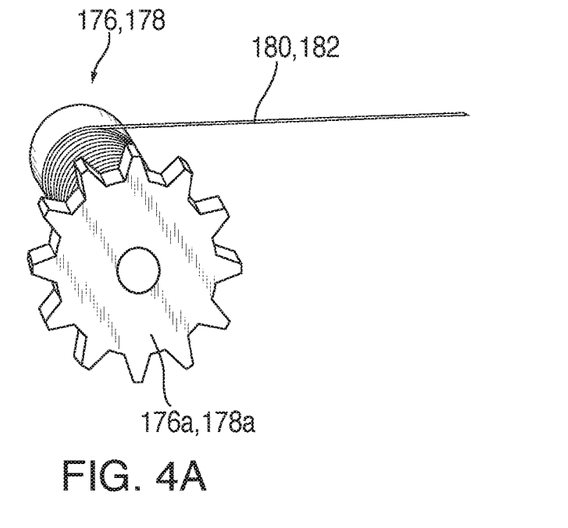
FIG. 4A is an enlarged perspective view of a pulley member of the adapter assembly shown in FIG. 1.
Figure 4B:
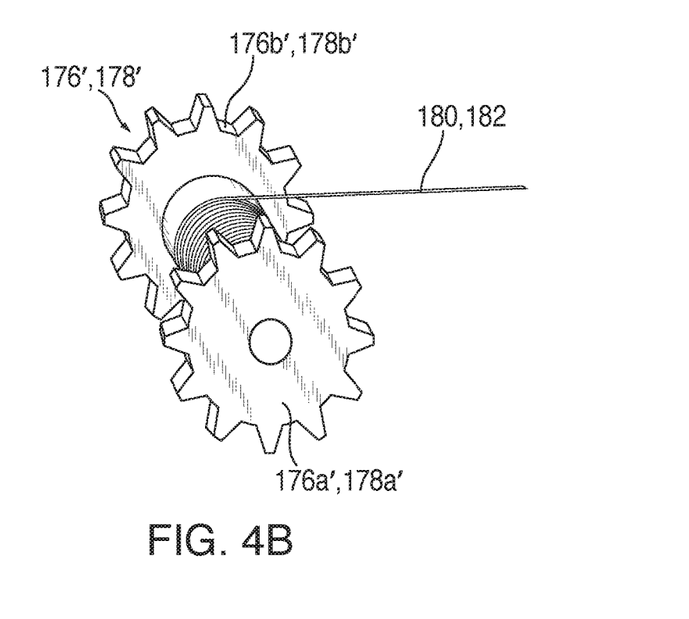
FIG. 4B is an enlarged perspective view of an alternative embodiment of a pulley member of the adapter assembly shown in FIG. 1.

The first and second pulley members 176, 178 of the pusher assembly 170 of the loading unit 150 are rotatably supported within the shell member 152 of the loading unit 150. Each of the first and second pulley members 176, 178 includes a first gear 176a, 178a (FIG. 4A) operably engageable with the plurality of notches 171 of the pusher member 172. In an alternative embodiment, first and second pulley members 176', 178' (FIG. 4B) include a first gear 176a', 178a', respectively, and a second gear 176b', 178b', respectively. As will be described in further detail below, rotation of the first and second pulley members 176, 178 causes corresponding longitudinal movement of the pusher member 172.

A first end of each of the first and second connectors 180, 182 is wound about the respective first and second pulley members 176, 178 and a second end of the first and second connectors 180, 182 is secured to the puller member 174 of the pusher assembly 170. The number of turns that the first and second connectors 180, 182 are wound about the respective first and second pulley members 176, 178 is such that during a stroke produced by the second drive assembly 130, the first and second pulley members 176, 178 are rotated sufficiently to effect the second function of the adapter assembly 100, e.g., advancement of the pusher member 172 to cause the stapling and cutting of tissue (not shown).

Figure 5:
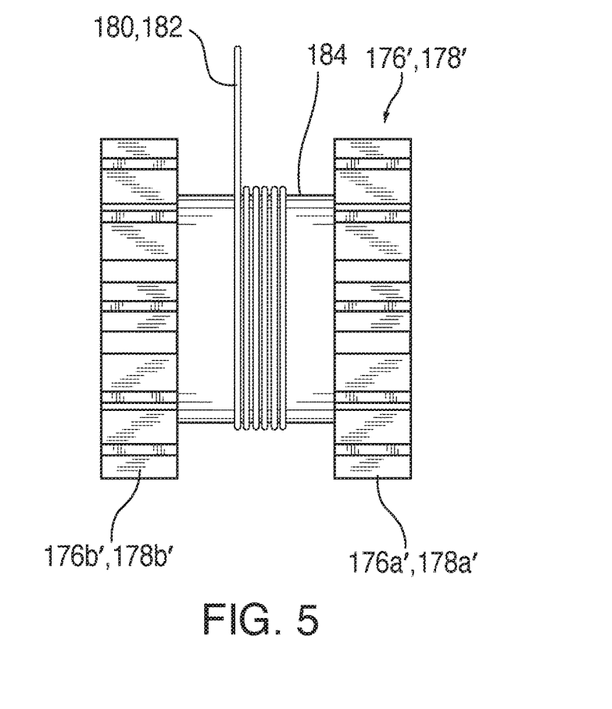
FIG. 5 is a top plan view of the pulley member shown in FIG. 4B.
Figure 6:
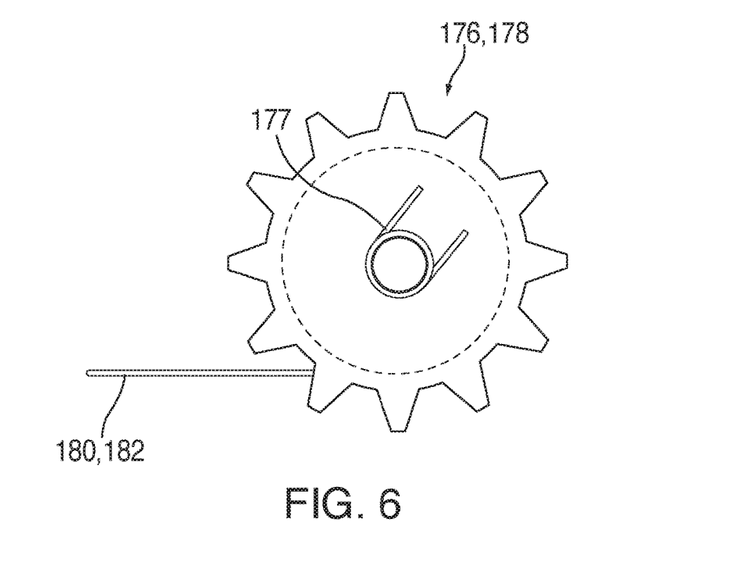
FIG. 6 is a side view of the pulley member shown in FIG. 4A, optionally including a torsion spring.

To prevent the first and second connectors from prematurely unwinding from the respective first and second pulley members 176, 178, and/or to maintain the tension on the first and second pulley members 176, 178, the first and second connectors 180, 182 may be secured to the respective first and second pulley members 176, 178 using a low durometer coating, i.e., rubber, or a break-away adhesive 184 (FIG. 5). Alternatively, the first and second pulley members 176, 178 may each include a torsion spring 177 (FIG. 6) for maintaining tension of the respective first and second connectors 180, 182. The torsion springs 177 cause the respective first and second pulley members 176, 178 to rotate in an opposite direction to cause the retraction of the pusher member 172 of the pusher assembly 170 and uptake of the respective first and second connectors 180, 182.

Figure 7:
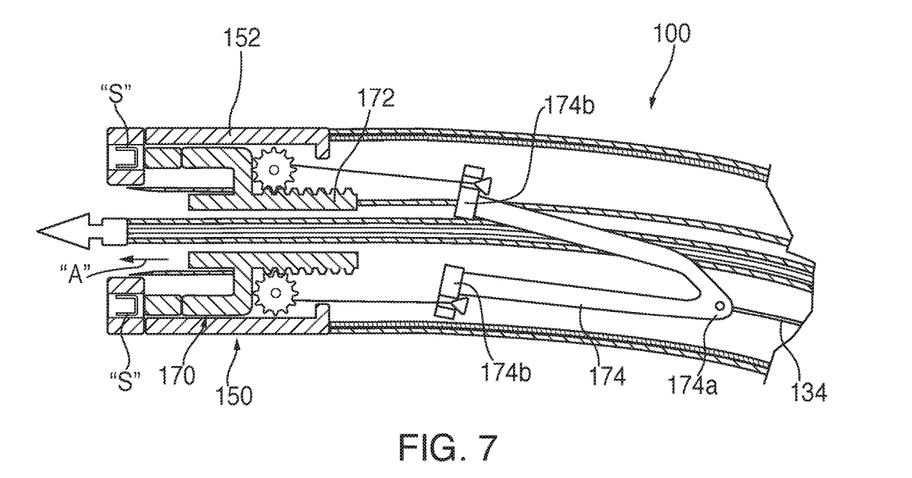
FIG. 7 is a side cross-sectional schematic view of the distal end of the adapter assembly and loading unit shown in FIG. 1, with a trocar member of a trocar assembly in an advanced position and a pusher member of a pusher assembly in a retracted position.

The operation of the adapter assembly 100 will now be described with reference to FIGS. 7-9. Referring initially to FIG. 7, the adapter assembly 100 is shown with the trocar member 162 of the trocar assembly 160 in an advanced position. The adapter assembly 100 may be provided to the clinician with the trocar member 162 in the advanced position. Alternatively, the trocar member 162 is provided to the clinician in a retracted position (FIG. 9), and is moved to the advanced position, as indicated by arrow "A", through operation of the first drive assembly 120 (FIG. 2). More particularly, rotation of the first screw member 126 (FIG. 2) of the first drive assembly 120 (FIG. 2) in a first direction, e.g., clockwise, causes the first carriage member 128 (FIG. 2) to move distally, e.g., advance relative to the first screw member 126, to push the the first push/pull cable 124. The trocar member 162 is secured to the first push/pull cable 124 such that the trocar member 162 is advanced with the first push/pull cable 124. When in the advanced position, the trocar member 162 of the trocar assembly 160 is configured to penetrate tissue and/or to facilitate attachment of the anvil assembly 30 to the adapter assembly 100.

The tissue to be stapled (not shown), is next positioned about the anvil assembly 30 (FIG. 8) and about the trocar member 162 of the trocar assembly 162 in a traditional manner. The anvil assembly 30 is then secured to the trocar member 162. The anvil assembly 30 (FIG. 8) may secure to the trocar member 162 in any suitable manner. In embodiments, retraction of the trocar member 162 locks the anvil assembly 30 to the trocar member 162 to prevent separation of the anvil assembly 30 from trocar member 162.

Figure 8:
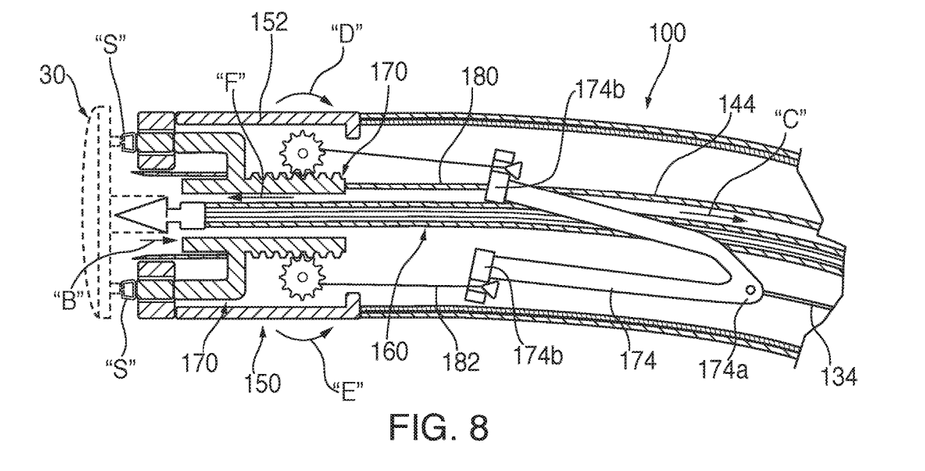
FIG. 8 is a side cross-sectional schematic view of the distal end of the adapter assembly and loading unit shown in FIG. 1, with an anvil assembly secured to the trocar member, the trocar member in an retracted position, and the pusher member in an advanced position.

With particular reference now to FIG. 8, the adapter assembly 100 is shown with the anvil assembly 30 secured to the trocar member 162 of the trocar assembly 160, and the trocar member 160 in the retracted position. The trocar member 160 is moved to the retracted position through operation of the first drive assembly 120 (FIG. 2). In particular, rotation of the first screw member 126 (FIG. 2) of the first drive assembly 120 (FIG. 2) in a second direction, e.g., counter-clockwise, causes the first carriage member 128 (FIG. 2) to move in a proximal direction, e.g., retract relative to the first screw member 126, to pull the first push/pull cable 124. Retraction of the first push/pull cable 124 causes the trocar member 162 to move in the proximal direction, e.g., retract into the loading unit 150, as indicated by arrow "B". As noted above, when in the retracted position, the anvil assembly 30 may be locked to the trocar member 162 to prevent separation of the anvil assembly 30 from the trocar member 162 during operation of the adapter assembly 100.

The pusher member 172 of the pusher assembly 170 is moved to the advanced position through operation of the second drive assembly 130. More particularly, rotation of the second screw member 136 (FIG. 2) of the second drive assembly 130 (FIG. 2) in a first direction, e.g., clockwise, causes the second carriage member 138 (FIG. 2) to move in a proximal direction, e.g., retract relative to the second screw member 136, to pull the second cable 134. Pulling of the second cable 134 causes retraction of the puller member 174 of the pusher assembly 170.

With continued reference to FIG. 8, retraction of the puller member 174 in the proximal direction, as indicated by arrow "C", causes the first and second connectors 180, 182 to unwind from the respective first and second pulley members 176, 178. As the first and second pulley members 176, 178 rotate in response to the respective first and second connectors 180, 182 being unwound therefrom, as indicated by arrows "D" and "E", respectively, the first gears 176a, 178a of the respective first and second pulley members 176, 178 engage the pusher member 172 to move the pusher member 172 in a distal direction, e.g., to the advanced position, as indicated by arrow "F", to eject the staples "S" from the staple cartridge 152 and to form the staple "S" against the anvil assembly 30 to staple tissue (not shown) and advance circular knife 175 to cut tissue (not shown). It is envisioned that the circular knife 175 of the pusher assembly 170 may be separate and independent from the pusher member 172. In this manner, the cutting function of the adapter assembly 100 may be performed independent of the stapling function of the adapter assembly 100.

Figure 9:
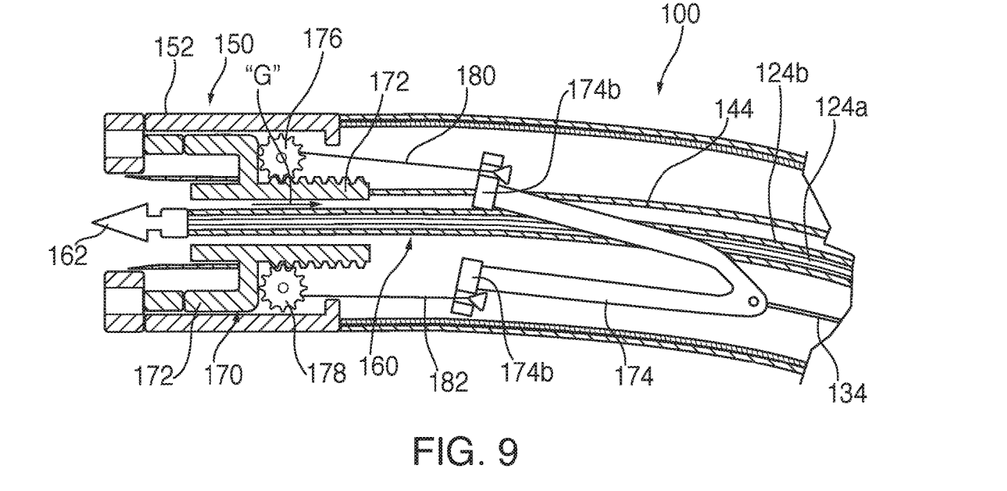
FIG. 9 is a side cross-sectional schematic view of the distal end of the adapter assembly and loading unit shown in FIG. 1, with the trocar member in the advanced position and the pusher member in the retracted position.

Turning now to FIG. 9, subsequent to the tissue (not shown) being stapled, the trocar member 162 of the trocar assembly 160 is advanced (FIG. 7), in the manner described above, to permit separation of the anvil assembly 30 (FIG. 8) therefrom. Prior to, simultaneous with, or subsequent to, the anvil assembly 30 being separated from the trocar member 162, the pusher member 172 of the pusher assembly 170 is moved distally to the retracted position, as indicated by arrow "G".

As shown, the pusher member 172 is moved to the retracted position through operation of the third drive assembly 140. In particular, rotation of the third screw member 146 (FIG. 2) of the third drive assembly 140 (FIG. 2) in a first direction, e.g., clockwise, causes the third carriage member 148 (FIG. 2) to move in a proximal direction, i.e., retract relative to the third screw member 146, to pull the third cable 144. Pulling of the third cable 144 causes retraction of the pusher member 172. To permit retraction of the pusher member 172, the first and second pulley members 176, 178 must be free to rotate in the opposite direction, or be configured to disengage the pusher member 172 subsequent to advancement of the pusher member 172.

Alternatively, the pusher assembly 170 may include a spring member (not shown) or other biasing member for returning the pusher member 172 to the initial, retracted position. In this manner, advancement of the pusher member 172 compresses the spring such that release of the tension on the first and second connectors 180, 182 allows the pusher member 172 to retract. As noted above, the springs that may be incorporated into the first and second pulley members 176, 178 may be torsion springs 177 (FIG. 6), or in any other suitable manner.

Following the surgical procedure, the adapter assembly 100 may be separated from the actuation assembly 20 and disposed of in a traditional manner. Alternatively, the adapter assembly 100 may be sterilized and reused. As noted above, the cartridge assembly 152 and/or the loading unit 150 may be replaceable, thereby permitting reuse of the adapter assembly 100.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly comprising:
a pusher assembly including a pusher member, a puller member for retracting the pusher member, and an activation assembly operably disposed between the pusher member and the puller member, the activation assembly including at least one pulley member;
a trocar assembly including a trocar member operably disposed relative to the pusher assembly;
a first drive assembly including a first cable for advancing and retracting the trocar member relative to the pusher assembly; and
a second drive assembly including a second cable for retracting the puller member to cause activation of the activation assembly, wherein activation of the activation assembly causes advancement of the pusher member.

2. The adapter assembly of claim 1, wherein the activation assembly includes first and second pulley members.

3. The adapter assembly of claim 2, wherein the first and second pulley members are connected to the puller member by respective first and second connectors.

4. The adapter assembly of claim 3, wherein the first and second connectors are wrapped around the respective first and second pulley members prior to advancement of the pusher member.

5. The adapter assembly of claim 4, wherein each of the first and second pulley members includes a coating for maintaining tension on the respective first and second connectors.

6. The adapter assembly of claim 4, wherein each of the first and second pulley members includes a torsion spring for maintaining tension on the respective first and second connectors.

7. The adapter assembly of claim 2, wherein each of the first and second pulley members includes a least a first gear for engaging the pusher member.

8. The adapter assembly of claim 1, wherein the pusher member is configured to staple tissue upon the advancement thereof.

9. The adapter assembly of claim 1, wherein the trocar member is releasably securable to an anvil assembly.

10. The adapter assembly of claim 1, further including a third drive assembly including a third cable connected to the pusher member.

11. The adapter assembly of claim 10, wherein the third drive assembly is configured to cause retraction of the pusher member upon operation thereof.

12. The adapter assembly of claim 1, further including an elongate body and a coupling assembly supported on a proximal end of the elongate body.

13. The adapter assembly of claim 12, further including a loading unit supported on a distal end of the elongate body.

14. The adapter assembly of claim 13, wherein the loading unit includes a staple cartridge supporting a plurality of staples.

15. The adapter assembly of claim 12, wherein at least a portion of the elongate body is flexible.

16. The adapter assembly of claim 12, wherein the elongate body includes an inner flexible coil and an outer sheath.

17. A circular stapler comprising:
an actuation assembly; and
the adapter assembly of claim 1 operably secured to the actuation assembly.

18. An adapter assembly comprising:
a pusher assembly including a pusher member, a puller member for retracting the pusher member, and an activation assembly operably disposed between the pusher member and the puller member, the activation assembly including at least one pulley member; and
a first drive assembly including a first cable for retracting the puller member to cause activation of the activation assembly, wherein activation of the activation assembly causes advancement of the pusher member.

* * * * *